United States Patent
Law et al.

(10) Patent No.: US 9,005,677 B2
(45) Date of Patent: Apr. 14, 2015

(54) AUTOPHAGY ENHANCER FOR TREATMENT OF NEURODEGENERATIVE DISEASES

(71) Applicant: Macau University of Science and Technology, Macau (CN)

(72) Inventors: Yuen Kwan Law, Macau (CN); An Guo Wu, Macau (CN); Kam Wai Wong, Macau (CN); Liang Liu, Macau (CN)

(73) Assignee: Macau University of Science and Technology, Macau ( * ) Notice: Subject to any disclaimer, the term of this patent is extended or adjusted under 35 U.S.C. 154(b) by 0 days.

(21) Appl. No.: 14/231,671

(22) Filed: Mar. 31, 2014

(65) Prior Publication Data

US 2015/0050363 A1 Feb. 19, 2015

Related U.S. Application Data

(60) Provisional application No. 61/866,045, filed on Aug. 15, 2013.

(51) Int. Cl.
*A01N 65/00* (2009.01)
*A61K 36/69* (2006.01)

(52) U.S. Cl.
CPC ...................................... *A61K 36/69* (2013.01)

(58) Field of Classification Search
CPC ..................................................... A61K 36/00
USPC ........................................................ 424/725
See application file for complete search history.

(56) References Cited

PUBLICATIONS

Levine B., Kroemer G., "Autophagy in the pathogenesis of disease", Cell, 2008, 132(1): 27-42.
Law B.Y.K., et al., "A novel inhibitor of the sarcoplasmic/endoplasmic reticulum Ca(2+) ATPase pump, induces autophagy, endoplasmic reticulum stress, and apoptosis", Molecular Cancer Therapeutics, 2010, 9(3): 718-730.
Rubinsztein D.C., "The roles of intracellular protein-degradation pathways in neurodegeneration", Nature. 2006, 443 (7113): 780-786.
Rubinsztein D.C., et al., "Autophagy and its possible roles in nervous system diseases, damage and repair", Autophagy, 2005, 1(1): 11-22.
Rubinsztein D.C., et al., "Potential therapeutic applications of autophagy", Nat. Rev. Drug Discov., 2007, 6 (4): 304-312.
Ravikumar B., Duden R., Rubinsztein D C., "Aggregate-prone proteins with polyglutamine and polyalanne expansions are degraded by autophagy", Hum. Mol. Genet., 2002, 11(9): 1107-1117.
Ravikumar B., et al., "Inhibition of mTOR induces autophagy and reduces toxicity of polyglutamine expansions in fly and mouse models of Huntington disease", Nat. Genet., 2004, 36 (6): 585-595.
Webb J.L., et al., "Alpha-Synuclein is degraded by both autophagy and the proteasome", J. Biol. Chem., 2003, 278 (27): 25009-25013.
Rubinsztein D.C., Codogno P., Levine B., "Autophagy modulation as a potential therapeutic target for diverse diseases", Nat. Rev. Drug Discov., 2012, 11(9): 709-730.
Rubinsztein D.C., "Lessons from animal models of Huntington's disease", Trends in Genetics, 2002, 18 (4): 202-209.
Sarkar S., et al., "Trehalose, a novel mTOR-independent autophagy enhancer, accelerates the clearance of mutant huntingtin and alpha-synuclein", J. Biol. Chem., 2007, 282 (8): 5641-5652.
Sarbar S., et al., "Lithium induces autophagy by inhibiting inositol monophosphatase", J. Cell Biol., 2005,170 (7): 1101-1111.
Berger Z., et al., "Rapamycin alleviate toxicity of different aggregate-prone proteins", Hum. Mol. Genet., 2006 15 (3): 433-442.
Wong E., Cuervo. A. M., "Autophagy gone awry in neurodegenerative diseases", Nat. Neurosci., 2010, 13 (7): 805-811.
Renna M., Jimenez-Sanchez M., Sarkar S., Rubinsztein D.C., "Chemical inducers of autophagy that enhance the clearance of mutant proteins in neurodegenerative diseases", J. Biol. Chem., 2010: 285 (15): 11061-11067.
Jia K., Levine B., "Autophagy is required for dietary restriction-mediated life span extension in *C. elegans*", Autophagy, 2007. 3 (6): 597-599.
Jia K., Hart A.C., Levine B., "Autophagy genes protect against disease caused by polyglutamine expansion proteins in *Caenorhabditis elegans*", Autophagy, 2007, 3(1): 21-25.
Komatsu M., et al., "Loss of autophagy in the central nervous system causes neurodegeneration in mice", Nature, 2006; 441(7095): 880-884.
Hara T., et al., "Suppression of basal autophagy in neural cells causes neurodegenerative disease in mice", Nature, 2006, 441 (7095): 385-889.
Komatsu M., et al., "Essential role for autophagy protein Atg7 in the maintenance of axonal homeostasis and the prevention of axonal degeneration", Proc .Natl Acad. Sci. U.S.A., 2007, 104 (36): 14489-14494.
Yang F., et al., "Curcumin inhibits formation of amyloid beta oligomers and fibrils, binds plaques, and reduces amyloid in vivo", J. Biol. Chem., 2005, 280 (7): 5892-5901.

(Continued)

*Primary Examiner* — Michael Meller
(74) *Attorney, Agent, or Firm* — Eagle IP Limited; Jacqueline C. Lui

(57) ABSTRACT

Use and application of Onjisaponin B derived and isolated from Radix Polygalae as novel autophagy enhancer are provided. A method of preventing, treating and/or delaying the onset of neurodegenerative diseases comprising administering an effective amount of Onjisaponin B is also provided.

1 Claim, 13 Drawing Sheets

(56) References Cited

PUBLICATIONS

Zhao Z., et al., "Potential antiarrhythmic effect of methyl 3,4,5-trimethoxycinnamate, a bioactive substance from roots of polygaiae radix: suppression of triggered activities in rabbit myocytes", Biol. Pharm. Bull., 2013, 36 (2): 238-244.

Zhang H., et al, "Effects of tenuifolin extracted from radix polygalae on learning and memory: a behavioral and biochemical study on aged and amnesic mice", Phytomedicine, 2008, 15 (8): 587-594.

Lin Z., Gu J., Xiu J., Mi T., Dong J., Tiwari J.K., "Traditional chinese medicine for senile dementia", Evid. Based Complement. Alternat. Med., 2012, 692621.

Choi J.G., et al., "Polygalae radix inhibits toxin-induced neuronal death in the Parkinson's disease models", J. Ethnopharmacol., 2011,134 (2): 414-421.

Karakida F., et al., "Cerebral protective and cognition-improving effects of sinapic acid in rodents", Biol. Pharm. Bull., 2007, 30 (3): 514-519.

Wong V.K. W., Zhou H., Cheung S.S.F., Li T., Liu L., "Mechanistic study of saikosaponin-d (Ssd) on suppression of murine T lymphocyte activation", J. Cell. Biochem., 2009, 107 (2): 303-315.

Sarkar S., et al., "Small molecules enhance autophagy and reduce toxicity in Huntington's disease models", Nat. Chem. Biol., 2007, 3(6): 331-338.

Talloczy Z., et al., "PKR-dependent autographic degradation of herpes simplex virus type 1", Autophagy, 2006, 2 (1): 24-29.

Outeiro T.F., et al., "Formation of toxic oligomeric alpha-synuclein species in living cells", PLoS One, 2008, 3(4): e1867.

Lu J.H., et al., "Baicalein inhibits formation of alpha-synuclein oligomers within living cells and prevents Abeta peptide fibrillation and oligomerisation", Chembiochem, 2011,12 (4): 615-624.

An-Gua Wu, et al., "Onjisaponin B, an autophagy enhancer isolated from the Radix Polygalae, accelerates the degradation of mutant α-synuclein and huntingtin, and reduces alpha-synuclein oligomerization in vitro", Int. J. Mol. Sci., 2013, 14, doi:10.3390.

An-Gua Wu, et al., "Onjisaponin B Derived from Radix Polygalae Enhances Autophagy and Accelerates the Degradation of Mutant α-Synuclein and Huntingtin in PC-12 Cells", Int. J. Mol. Sci., 2013 (revised), 14, doi:10.3390.

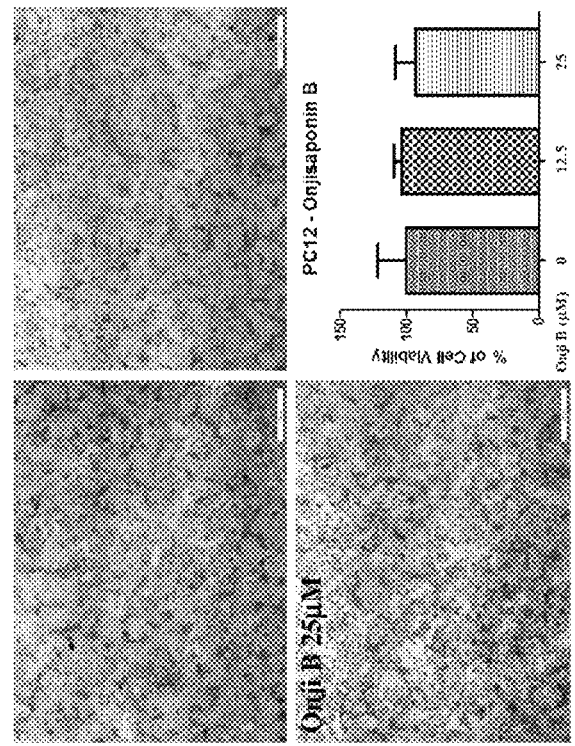
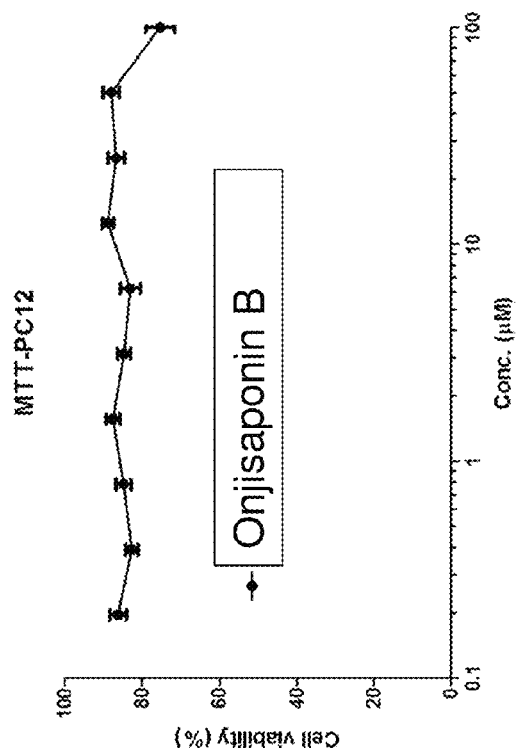
Figure 2a
Figure 2b

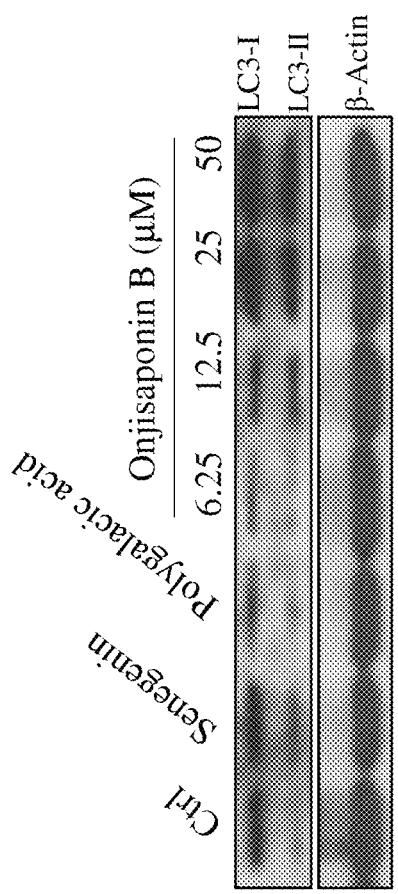
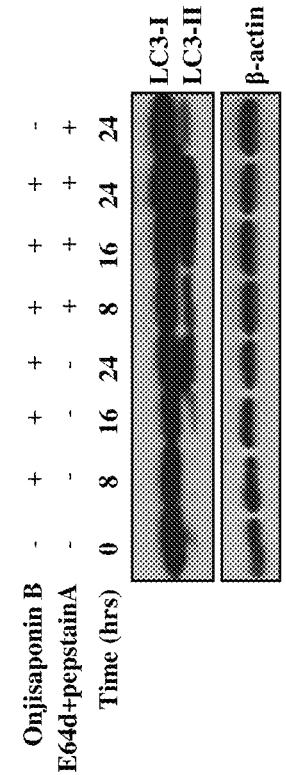
Figure 3b
Figure 3c

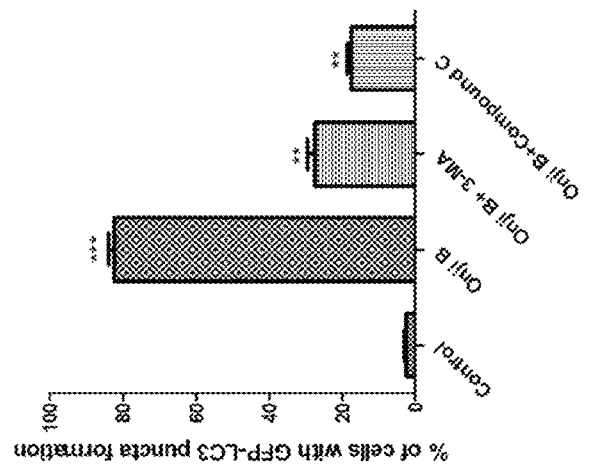
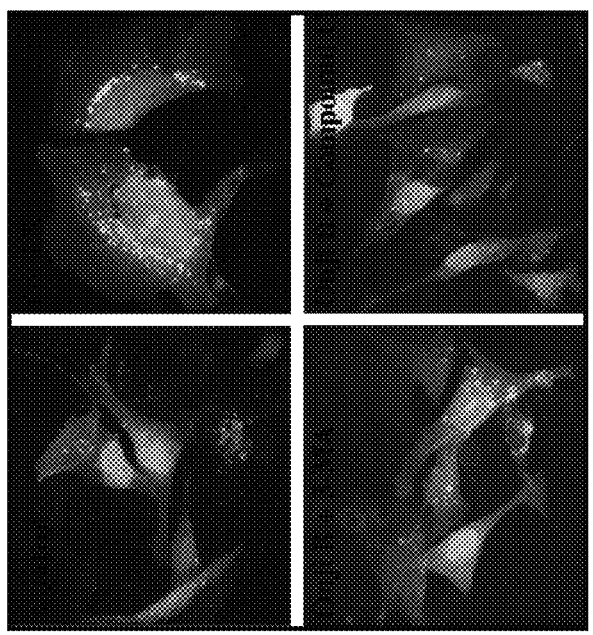
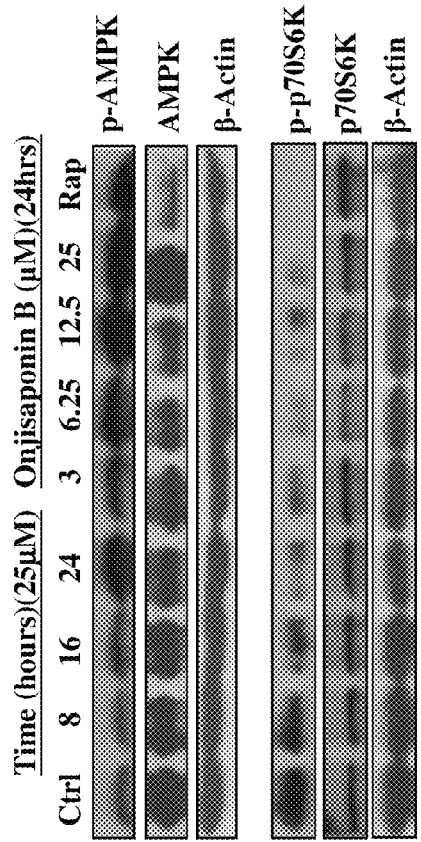
Figure 5a
Figure 5b

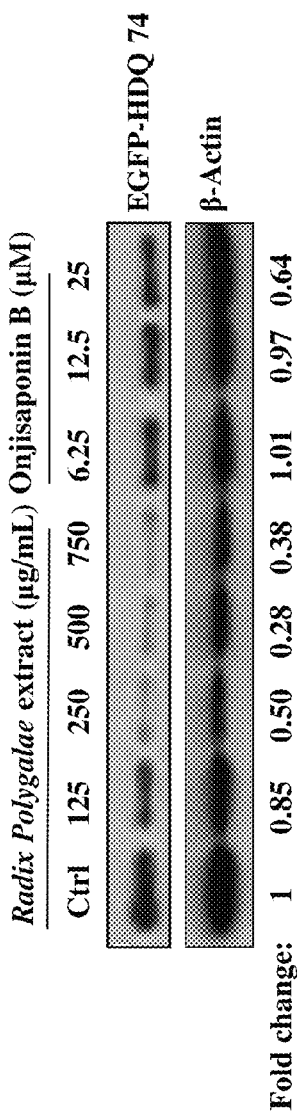
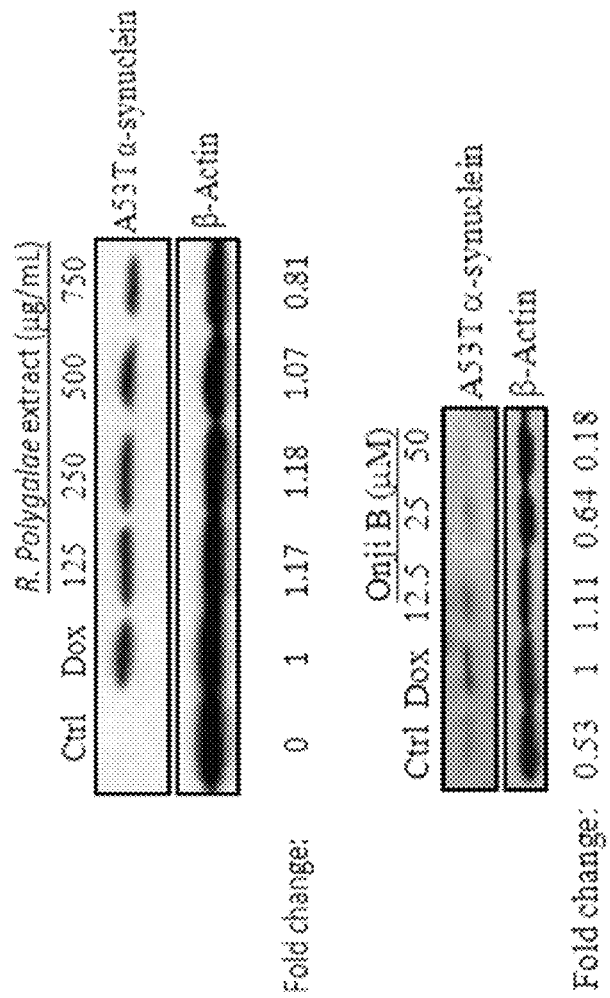
Figure 6a
Figure 6b

AUTOPHAGY ENHANCER FOR TREATMENT OF NEURODEGENERATIVE DISEASES

CROSS-REFERENCE TO RELATED APPLICATION

This application claims benefit under 35 U.S.C. §119(e) of U.S. Provisional Application having Ser. No. 61/866,045 filed 15 Aug. 2013, which is hereby incorporated by reference herein in its entirety.

FIELD OF INVENTION

This invention relates to a novel autophagy enhancer and the use thereof in treating neurodegenerative diseases.

BACKGROUND OF INVENTION

Autophagy is a cellular process that involves the formation of an isolated membrane to form double membrane vesicles (autophagosomes) that sequesters the cytoplasmic materials. Followed by fusion of the autophagosome with lysosome to form an autolysosome, all the engulfed materials are degraded by lysosomal hydrolases to recycle intracellular nutrients and energy [1, 2]. Autophagy-lysosome and ubiquitin-proteasome pathways are the two major protein degradation pathways in cells [3]. While short-lived nuclear and cytosolic proteins are degraded by proteasomes, large membrane proteins, oligomers and aggregates which cannot pass through the narrow pore of the proteasome barrel are degraded by autophagy [4].

A variety of neurodegenerative diseases are caused by toxic, aggregate-prone or oligomeric proteins [5-9]. For example, Huntington's disease (HD) is caused by an over 35 CAG trinucleotide repeat expansion, which results in a long mutant polyQ tract in the huntingtin protein. These polyQ expansions are highly associated with the aggregate formation and toxicity [10, 11]. Autophagy, however, can reduce mutant huntingtin protein levels and its toxicity in cell and mouse models [6, 7]. Parkinson disease (PD) is caused by A53T or A30P α-synuclein mutants, which are identified as substrates of autophagy, and the clearance of these mutant proteins are also highly dependent on autophagy for removal [6-8, 11-14]. Pharmacological activation of autophagy reduces the levels and toxicity of mutant huntingtin, mutant proteins in spinocerebellar ataxia, mutant α-synuclein and mutant tau in either mouse or drosophila models [5, 15]. Furthermore, autophagy-related gene (ATG) knockdown leads to aggregate formation and toxicity in C.elegans [16, 17]. In addition to the formation of protein aggregates, the accumulation of abnormal mitochondria or endoplasmic reticulum, and an increase in the size and number of lipid droplets were observed in ATG gene knockout animal models [14, 18-20].

SUMMARY OF INVENTION

In the light of the foregoing background, it is an object of the present invention to provide a novel autophagy enhancer with potential therapeutic application in neurodegenerative diseases by enhancing the clearance of mutant huntingtin and α-synuclein, and reduces α-synuclein oligomerization. As a result, the autophagy enhancer is able to recover from mutant huntingtin or α-synuclein-induced neuronal cell death.

In the first aspect, the present invention relates to a method of preventing, treating and/or delaying the onset of neurodegenerative diseases comprising administering an effective amount of Onjisaponin B to a subject in need thereof.

In one embodiment, Onjisaponin B is isolated from Chinese medicinal herbs, Radix Polygalae.

In another embodiment, the neurodegenerative diseases are caused by the buildup of oligomeric proteins comprising mutant huntingtin and mutant α-synuclein.

In yet another embodiment, the neurodegenerative diseases are selected from a group consisting of Parkinson's disease, and Huntington's disease.

In another aspect of this invention, a use of Onjisaponin B as an autophagy enhancer for treating neurodegenerative diseases is provided. In one embodiment, Onjisaponin B has been described in the foregoing paragraph(s); in another embodiment, the neurodegenerative diseases have also been described in the foregoing paragraph(s).

In yet another aspect, the present invention provides a pharmaceutical composition comprising Onjisaponin B admixed with a pharmaceutical carrier for treating neurodegenerative diseases. In one embodiment, Onjisaponin B has been described in the foregoing paragraph(s); in another embodiment, the neurodegenerative diseases have also been described in the foregoing paragraph(s).

In another aspect, the present invention provides a dietary supplement comprising Onjisaponin B admixed with a pharmaceutical carrier for treating neurodegenerative diseases. In one embodiment, Onjisaponin B has been described in the foregoing paragraph(s); in another embodiment, the neurodegenerative diseases have also been described in the foregoing paragraph(s).

The present invention is based on the identification of novel autophagy enhancer, Onjisaponin B as mentioned above. The invention is also based on the neuroprotective effect of Onjisaponin B on neuronal cells via enhancing the clearance of mutant huntingtin and α-synuclein, as well as preventing the oligomerization of α-synuclein.

Onjisaponin B exhibits no significant cytotoxic effect on a rat adrenal pheochromocytoma cells (PC 12) up to 100 μM. It is also relatively non-toxic to mouse, rat and human neuronal cells and brain tissues.

Onjisaponin B is a novel autophagy enhancer isolated from Radix Polygalae and has never been reported before. Also, Onjisaponin B is capable of inducing autophagy in cells and animals.

Onjisaponin B-induced autophagy is dependent on autophagy-related gene 7 (Atg7); further, Onjisaponin B is capable of inducing autophagy in Atg7-dependent manner Besides, Onjisaponin B induces autophagy via activation of AMP-activated protein kinase (AMPK) and inhibition of mammalian target of rapamycin (mTOR) signaling. Onjisaponin B is capable of inducing autophagy via modulation of AMPK-mTOR signaling pathway.

Further, Onjisaponin B enhances the clearance of mutant huntingtin and mutant A53T α-synuclein; further, Onjisaponin B is capable of enhancing the clearance of mutant huntingtin and mutant A53T α-synuclein.

Onjisaponin B enhances the clearance of mutant huntingtin in autophagy-wild type cells, but not in autophagy-deficient cells; further, Onjisaponin B is capable of enhancing the clearance of mutant huntingtin through autophagy induction.

Onjisaponin B reduces the oligomerization of α-synuclein; further, Onjisaponin B is capable of reducing the oligomerization of α-synuclein.

Onjisaponin B reduces toxicity in PC-12 cells expressing either mutant huntingtin or mutant A53T α-synuclein; further, Onjisaponin B is capable of recovering from the mutant huntingtin or mutant A53T α-synuclein-mediated toxicity in neuronal cells or tissues.

Onjisaponin B can be developed as novel neuroprotective agents for patients with neurodegenerative diseases.

BRIEF DESCRIPTION OF FIGURES

FIG. 2a and FIG. 2b show the results of cytotoxicity study of Onjisaponin B in PC12 cells.

FIG. 3a, FIG. 3b and FIG. 3c show that Onjisaponin B induces autophagic GFP-LC3 puncta formation, LC3-II conversion and autophagic flux in PC12 cells.

FIG. 5a and FIG. 5b show that Onjisaponin B activates autophagy through an AMPK-mTOR signaling pathway.

FIG. 6a and FIG. 6b show that Onjisaponin B enhances the clearance of mutant huntingtin and mutant A53T α-synuclein.

DETAILED DESCRIPTION OF THE PREFERRED EMBODIMENTS

Figure 1:
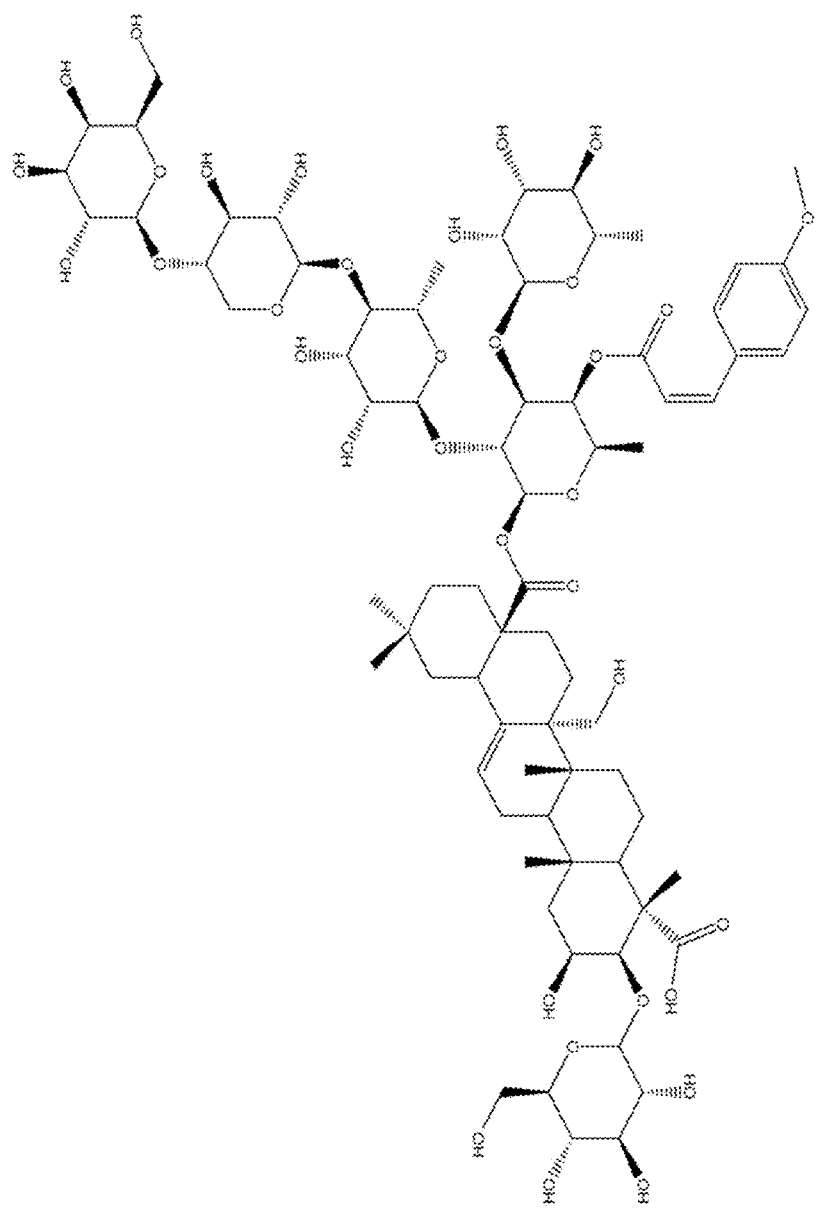
FIG. 1 shows the chemical structure of Onjisaponin B.

As used herein and in the claims, "comprising" means including the following elements but not excluding others.

In this study, novel autophagy enhancers with neuroprotective effects by evaluating their efficacy in enhancing the clearance of mutant huntingtin and α-synuclein, and in increasing of cells viability, are identified. Through screening of their library of natural product extracts from the Chinese medicinal herbs, inventors have demonstrated that both ethanol extract of Radix Polygalae and its single component, Onjisaponin B, are able to induce autophagy with potential therapeutic application in neurodegeneration.

The formula, molecular weight and accurate mass of Onjisaponin B are summarized in Table 1 below.

TABLE 1

| Chemical Name | Formula | Molecular Weight | Accurate MS |
|---|---|---|---|
| Onjisaponin B | $C_{75}H_{112}O_{35}$ | 1573.689 | 1572.698425 |

The reference cited throughout this application is identified in square bracket as "[xx]" with xx referring to the number of the corresponding reference on the "References" list.

The following preparations and examples are given to enable those skilled in the art to more clearly understand and to practice the present invention. They should not be considered as limiting the scope of the invention, but merely as being illustrative and representative thereof.

EXAMPLE 1

This example describes in vitro cytotoxicity of Onjisaponin B in a rat adrenal pheochromocytoma cells (PC12).

Cell culture and cytotoxicity assay: The test compound of Onjisaponin B was dissolved in DMSO at a final concentration of 100 mmol/L and stored at −20° C. Cytotoxicity was assessed using the 3-(4,5-dimethylthiazol-2-yl) -2,5-diphenyltetrazolium bromide assay as described previously [28]. PC-12, 4000 cells were seeded on 96-well plates per well. After overnight pre-incubation, the cells were exposed to different concentrations of Onjisaponin B (0.039-100 μmol/L) for 2 days. Subsequently, 10 μL of MTT reagents was added to each well and incubated at 37° C. for 4 hours followed by the addition of 100 μL solubilization buffer (10% SDS in 0.01 mol/L HCl) and overnight incubation. Absorbance at 585 nm was determined from each well the next day. For cell viability assay measured by crystal violet staining, PC-12 cells were incubated in 35 mm disc followed by the addition of Onjisaponin B at the indicated concentrations for 24 hours. The cells were then incubated with crystal violet for 10 minutes followed by a ddH$_2$O wash. The stained cells image was captured by CCD digital camera Spot RT3™ under the Nikon ECLIPSE 80i microscope with 4× magnification. Cell viability was quantified by dissolving the stained cells in 10% acetic acid (200 μL/well). The colorimetric reading of the solute mixture was then determined by spectrophotometer at OD 560 nm The percentage of cell viability was calculated using the following formula: Cell viability (%)=Cells number treated/Cells number DMSO control× 100. Data was obtained from three independent experiments.

Results: There was no toxicity observed overtly in PC-12 cells treated with Onjisaponin B for 48 hours as revealed by MTT assay as shown in FIG. 2a. Besides, no significant morphological damage was found in PC12 cells treated with Onjisaponin B for 24 hours as revealed by the crystal violet assay as shown in FIG. 2b.

Conclusion: The result shows that Onjisaponin B is non-toxic in rat adrenal pheochromocytoma cells (PC-12).

EXAMPLE 2

This example describes an in vitro study to demonstrate the autophagic effect of Onjisaponin B.

Quantification of autophagy GFP-LC3 Puncta. GFP-LC3 puncta formation was quantified as described previously [2]. In brief, cells grown on coverslips in a 6-well plate were fixed in 4% paraformaldehyde for 20 minutes at room temperature and then rinsed with PBS. Slides were mounted with Fluor-Save™ mounting media (Calbiochem, San Diego, Calif.) and examined by fluorescence microscopy. The number of GFP-positive cells with GFP-LC3 puncta formation was examined under the Nikon ECLIPSE 80i microscope. Representative images were captured with CCD digital camera Spot RT3™ (Diagnostic Instruments, Inc., Melville, N.Y.). To quantify autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields was scored.

Detection of autophagic marker protein LC3 conversion. After drug treatments with or without autophagy inhibitor (10 g/mL E64D and pepstain A), cells were harvested and lysed in RIPA buffer (Cell Signaling Technologies Inc., Beverly, Mass.). The cell lysates were then resolved by SDS-PAGE. After electrophoresis, the proteins from SDS-PAGE were transferred to nitrocellulose membrane which was then blocked with 5% non-fat dried milk for 60 minutes. The membrane was then incubated with LC3 primary antibodies (1:1000) in TBST overnight at 4° C. After that, the membrane was further incubated with HRP-conjugated secondary antibodies for 60 minutes. Finally, protein bands were visualized by using the ECL Western Blotting Detection Reagents (Invitrogen, Paisley, Scotland, UK).

Figure 3A:
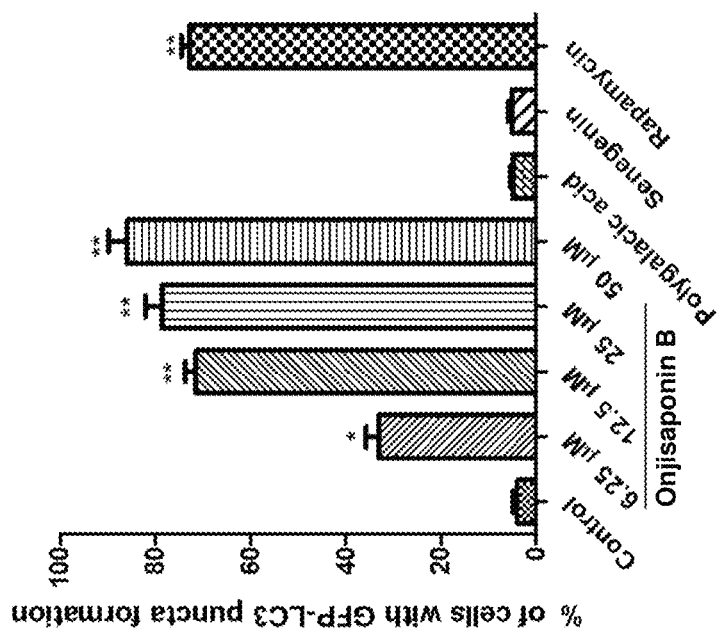
Figure 3A:
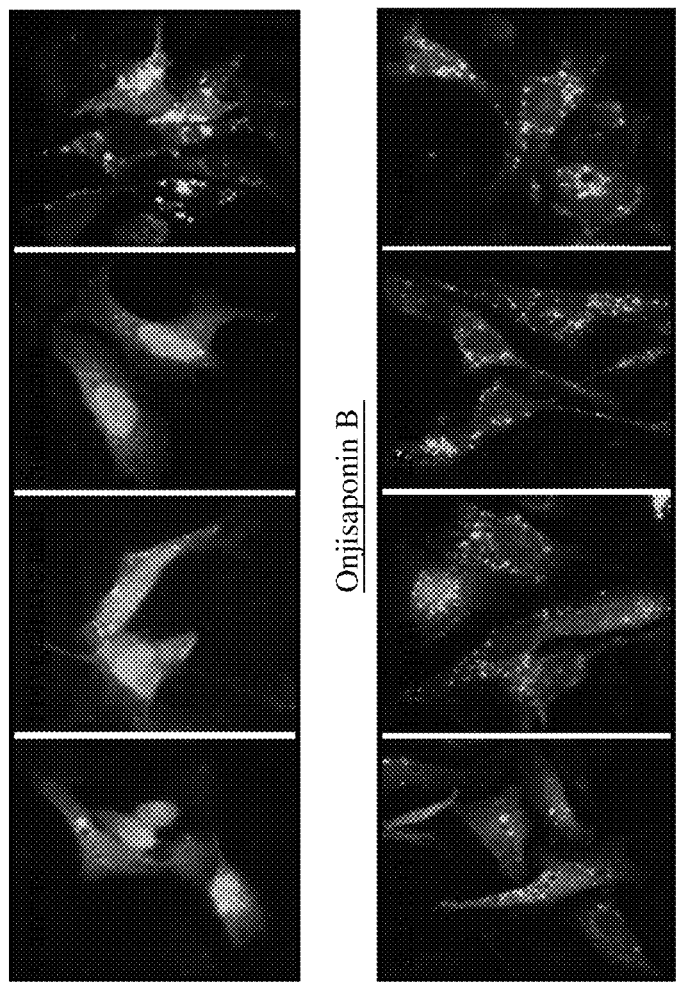

Results: The positive control drug, rapamycin, demonstrated a markedly increase in GFP-LC3 puncta formation. While the other active components of Radix Polygalae including polygalacic acid and senegenin showed no autophagy activity in cells, Onjisaponin B increased the formation of GFP-LC3 puncta formation in a dose dependent manner as revealed by fluorescent microscopy as shown in FIG. 3a. In addition, western blot analysis of autophagic marker LC3 also demonstrated the increase of LC3-II conversion upon Onjisaponin B treatment as shown in FIG. 3b. Furthermore, Onjisaponin B increased the rate of LC3-II formation in the presence of protease inhibitors as shown in FIG. 3c, suggesting that Onjisaponin B induces autophagic flux, rather than promotes the blockage of fusion between autophagosome and lysosome.

Conclusion: These data proved that Onjisaponin B has the autophagic effect and suggested that Onjisaponin B is a novel autophagy enhancer in Radix Polygalae.

EXAMPLE 3

This example describes an in vitro study to demonstrate the autophagic effect of Onjisaponin B is dependent on the presence of autophagy-related gene 7 (Atg7).

Quantification of autophagy GFP-LC3 Puncta in Atg7 wild type and deficient MEFs. GFP-LC3 puncta formation was quantified as described previously [2]. In brief, both Atg7 wild-type and deficient mouse embryonic fibroblasts (MEFs) grown on coverslips in a 6-well plate were treated with indicated concentrations of Onjisaponin B. The cells were then fixed in 4% paraformaldehyde for 20 minutes at room temperature and then rinsed with PBS. Slides were mounted with FluorSave™ mounting media (Calbiochem, San Diego, Calif.) and examined by fluorescence microscopy. The number of GFP-positive cells with GFP-LC3 puncta formation was examined under the Nikon ECLIPSE 80i microscope. Representative images were captured with CCD digital camera Spot RT3™ (Diagnostic Instruments, Inc., Melville, N.Y.). To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields was scored.

Figure 4:
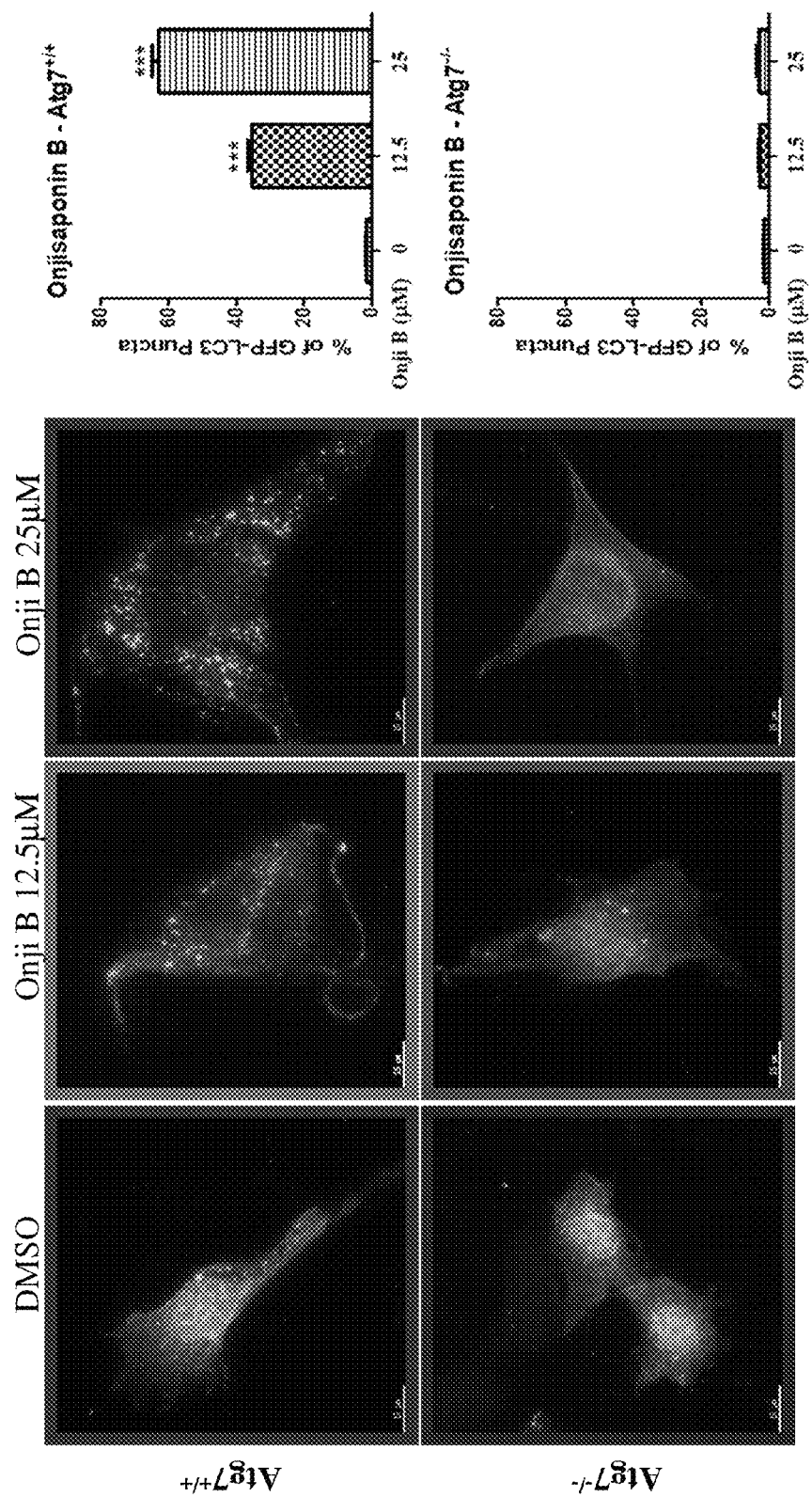
FIG. 4 shows that Onjisaponin B-induced autophagy is dependent on the presence of autophagy-related gene7 (Atg7).

Results: Onjisaponin B was found to induce GFP-LC3 puncta formation in wild type Atg7 cells but not in Atg7-knockout mouse embryonic fibroblasts as shown in FIG. 4.

Conclusion: The results show that Onjisaponin B works as a novel autophagy enhancer which depends on autophagy related gene, Atg7, for the induction of autophagy.

EXAMPLE 4

This example describes an in vitro study to demonstrate the molecular mechanism of Onjisaponin B in autophagy induction.

Detection of mTOR signaling marker proteins. PC12 cells treated with indicated time and concentrations of Onjisaponin B were harvested and lysed in RIPA buffer (Cell Signaling). The cell lysates were then resolved by SDS-PAGE. After electrophoresis, the proteins from SDS-PAGE were transferred to nitrocellulose membrane which was then blocked with 5% non-fat dried milk for 60 minutes. The membrane was then incubated with P-p70S6K, p70S6K, P-AMPK, AMPK primary antibodies (1:1000) in TBST overnight at 4° C. respectively. After that, the membrane was further incubated with HRP-conjugated secondary antibodies for 60 minutes. Finally, protein bands were visualized by using the ECL Western Blotting Detection Reagents (Invitrogen).

Quantification of Onjisaponin B-mediated autophagy in the presence of specific inhibitors. GFP-LC3 puncta formation was quantified as described previously [2]. In brief, PC12 cells expressing GFP-LC3 were treated with Onjisaponin B (Onji, 25 μM) in the presence of AMPK inhibitor (compound C) (CC, 5 μM) or 3-Methyladenine (3-MA, 5 mM) for 12 hours. The cells were then fixed in 4% paraformaldehyde for 20 minutes at room temperature and then rinsed with PBS. Slides were mounted with FluorSave™ mounting media (Calbiochem) and examined by fluorescence microscopy. To quantify for autophagy, the percentage of cells with punctate GFP-LC3 fluorescence was calculated by counting the number of the cells with punctate GFP-LC3 fluorescence in GFP-positive cells. A minimum of 150 cells from 3 randomly selected fields was scored.

Results: Onjisaponin B was found to activate the phosphorylation of AMPK in a time dependent manner (as observed from columns 2-4 of FIG. 5a that show the results of the study in which protein bands of 25 μM Onjisaponin B were visualized at the $8^{th}$, $16^{th}$ and $24^{th}$ hour) and dose dependent manner (as observed from columns 5-8 of FIG. 5a that show the results of the study in which protein bands of Onjisaponin B at concentrations of 3 μM, 6.25 μM, 12.5 μM and 25 μM were visualized at the $24^{th}$ hour), and this activation was also accompanied by a concomitant reduction in its downstream p70S6K phosphorylation. In addition, there was a significant reduction in Onjisaponin B-induced GFP-LC3 puncta formation in PC12 cells treated with the presence of AMPK inhibitor (compound C) or the autophagy inhibitor (3-Methyladenine,3-MA), which is a specific inhibitor of the class III PI3K responsible for autophagy induction as shown in FIG.5b.

Conclusion: The results show that Onjisaponin B activates autophagy through an AMPK-mTOR signaling pathway.

EXAMPLE 5

This example describes an in vitro study to demonstrate the clearance of mutant huntingtin and mutant A53T α-synuclein by Onjisaponin B.

Removal of mutant huntingtin and mutant α-synuclein. PC 12 cells were transfected transiently with EGFP-HDQ74 plasmids for 24 hours using Lipofectamine Plus LTX reagent (Invitrogen) according to the manufacturer's protocol. The transfected cells were then treated with Onjisaponin B for 24 hours. The removal of mutant huntingtin, EGFP-HDQ74, was then quantitated by immunoblotting with antibody against EGFP. To measure the clearance of α-synuclein in cellular model, the overexpression of mutant A53T α-synuclein was first induced by the addition of doxycycline (1 μg/ml) (Sigma) for 24 hours [11], by using the doxycycline inducible PC 12 cell line transfected with A53T α-synuclein plasmid. The expression of mutant A53T α-synuclein was then switched off by removing doxycycline from medium. Cells were then incubated with Onjisaponin B for a further 24 hours. The clearance of mutant α-synuclein was then measured by immunoblotting with antibody against myc tag.

Results: Both ethanol extract of Radix Polygalae and Onjisaponin B enhanced the clearance of overexpressed EGFP-tagged mutant huntingtin with 74 CAG repeats as measured by immunoblotting against EGFP antibody as shown in FIG. 6a. On the other hand, the expression of A53T α-synuclein can be switched on by adding the chemical agent, doxycycline. Upon the induction by doxycycline, whether specific compounds enhance the clearance of mutant proteins [11, 29, 30] can be evaluated. As shown in FIG. 6b, both Radix Polygalae ethanol extract and Onjisaponin B accelerate the clearance of myc-tagged mutant A53T α-synuclein, whereas cells without Onjisaponin B or ethanol extract incubation showed no removal of mutant protein after doxycycline induction. The fold change in both FIGS. 6a and 6b indicated the fold change of EGFP-HDQ 74 level.

Conclusion: The results show that Onjisaponin B works as a useful neuroprotective agent through accelerating the clearance of mutant huntingtin and α-synuclein in vitro.

EXAMPLE 6

This example describes an in vitro study to demonstrate that the clearance of mutant huntingtin by Onjisaponin B requires autophagy induction.

Quantification of mutant huntingtin aggregates in PC12, Atg7 wild type and deficient MEFs. In brief, both EGFP-HDQ74 transfected PC12, Atg7 wild-type and deficient mouse embryonic fibroblasts (MEFs) grown on coverslips in a 6-well plate were treated with indicated concentrations of Onjisaponin B. The cells were then fixed in 4% paraformaldehyde for 20 minutes at room temperature and then rinsed with PBS. Slides were mounted with FluorSave™ mounting media (Calbiochem, San Diego, Calif.) and examined by fluorescence microscopy. The number of cells with GFP-aggregates formation was examined under the Nikon ECLIPSE 80i microscope. Representative images were captured with CCD digital camera Spot RT3™ (Diagnostic Instruments, Inc., Melville, N.Y.). To quantify the clearance of mutant huntingtin, the percentage of cells with GFP-aggregates was calculated by counting the number of the cells with punctate GFP-LC3 fluorescence in GFP-positive cells. A minimum of 150 cells from 3 randomly selected fields was scored.

Detection of autophagic marker protein LC3 conversion and HTT 74 mutant aggregates. After drug treatments for Atg7 wild type and deficient MEFs, cells were harvested and lysed in RIPA buffer (Cell Signaling Technologies Inc., Beverly, Mass.). The cell lysates were then resolved by SDS-PAGE. After electrophoresis, the proteins from SDS-PAGE were transferred to nitrocellulose membrane which were then blocked with 5% non-fat dried milk for 60 minutes. The membrane was then incubated with LC3 primary antibodies (1:1000) in TBST overnight at 4° C. After that, the membrane was further incubated with HRP-conjugated secondary antibodies for 60 minutes. Finally, protein bands were visualized by using the ECL Western Blotting Detection Reagents (Invitrogen, Paisley, Scotland, UK).

Figure 7A:
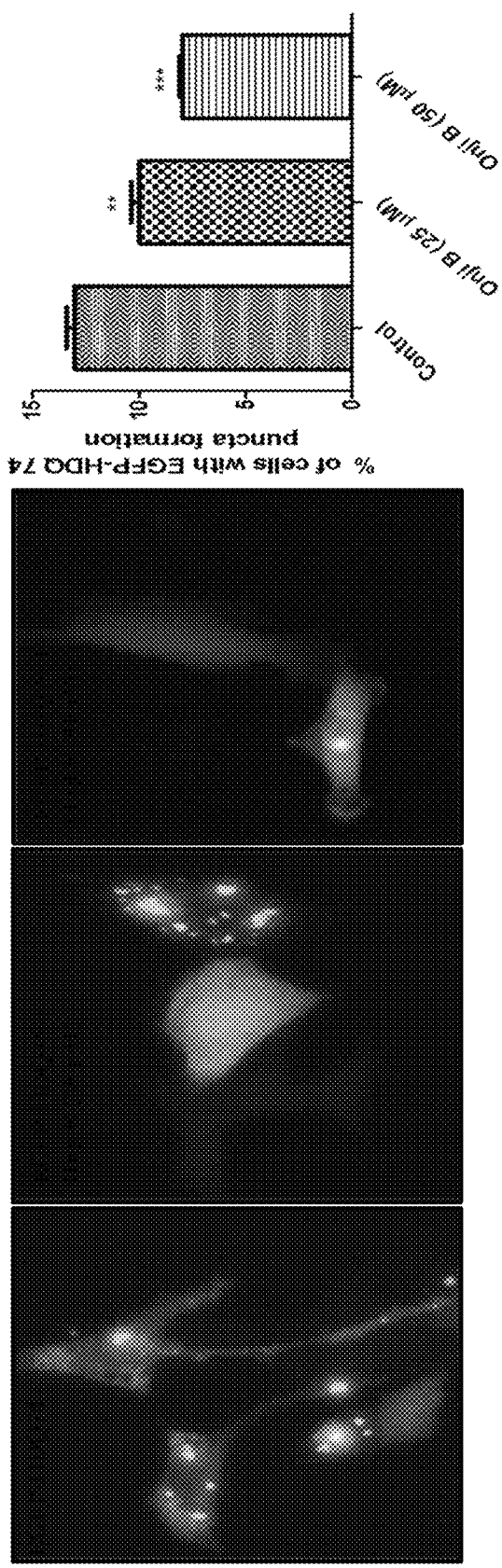
FIG. 7a, FIG. 7b and FIG. 7c show that Onjisaponin B enhances the clearance of mutant huntingtin in autophagy-wild type cells, but not in autophagy-deficient cells.
Figure 7B:
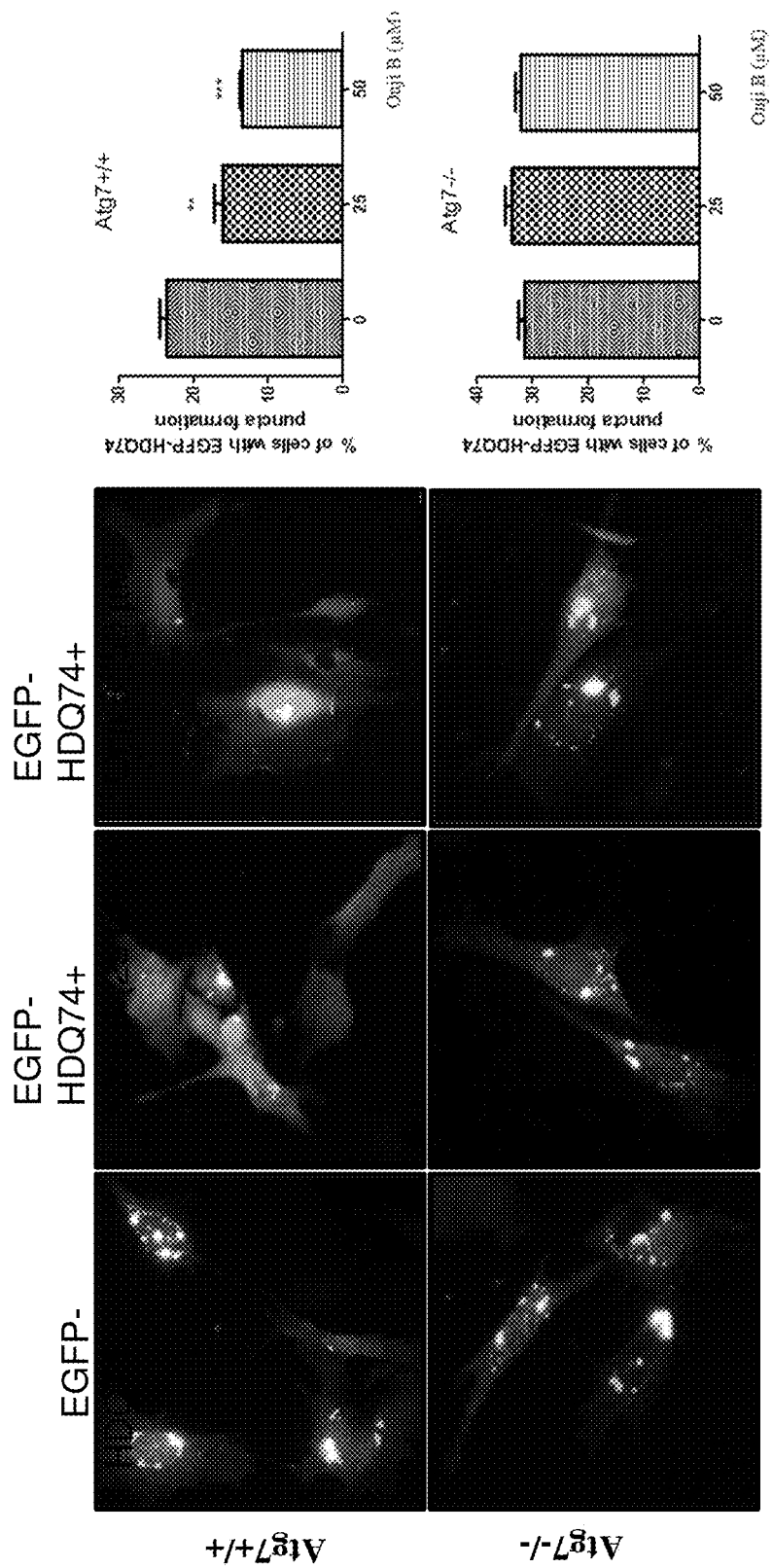
Figure 7C:
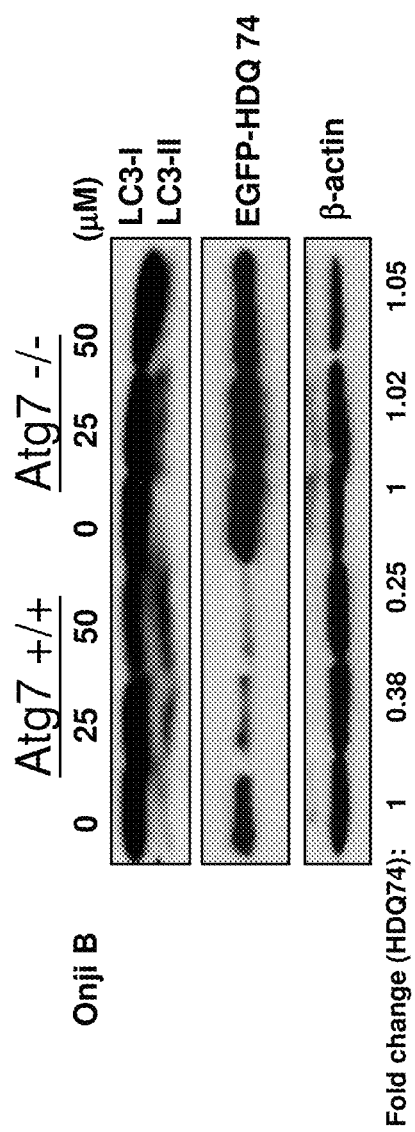

Results: Immunocytochemistry analysis further confirmed that Onjisaponin B enhanced the clearance of inclusions formed by EGFP-HDQ74 as shown in FIG. 7a. To further confirm that the protective effect of Onjisaponin B was due to an Atg7 dependent autophagic effect, wild type Atg7 and Atg7-knockout mouse embryonic fibroblasts were transfected with EGFP-HDQ74 for fluorescent inclusions formation. Results showed that Onjisaponin B enhanced the clearance of EGFP-HDQ74 inclusions as illustrated in FIG. 7b; further, as shown in FIG. 7c, the rate of LC3II formation in wild type Atg7 cells but not in Atg7-knockout cells suggested the compound-mediated neuroprotective effect was autophagy dependent.

Conclusion: The enhanced clearance of mutant huntingtin by Onjisaponin B requires the induction of autophagy in cells.

EXAMPLE 7

This example describes an in vitro study to demonstrate the reduced oligomerization of α-synuclein mediated by Onjisaponin B.

Bimolecular fluorescence complementation (BiFC) assay. In brief, HeLa cells transfected with both GFP-N terminal-α-synuclein (GNS) and α-synuclein-GFP-C terminal (SGC) plasmids were incubated at 37° C. for 4 hours. Then, the transfected cells were incubated with different concentrations of Radix Polygalae ethanol extract or Onjisaponin B for a further 24 hours at 30° C. [31]. Fluorescent signals upon complete GFP fluorophore reconstitution in cells were then detected by flow analysis.

Figure 8:
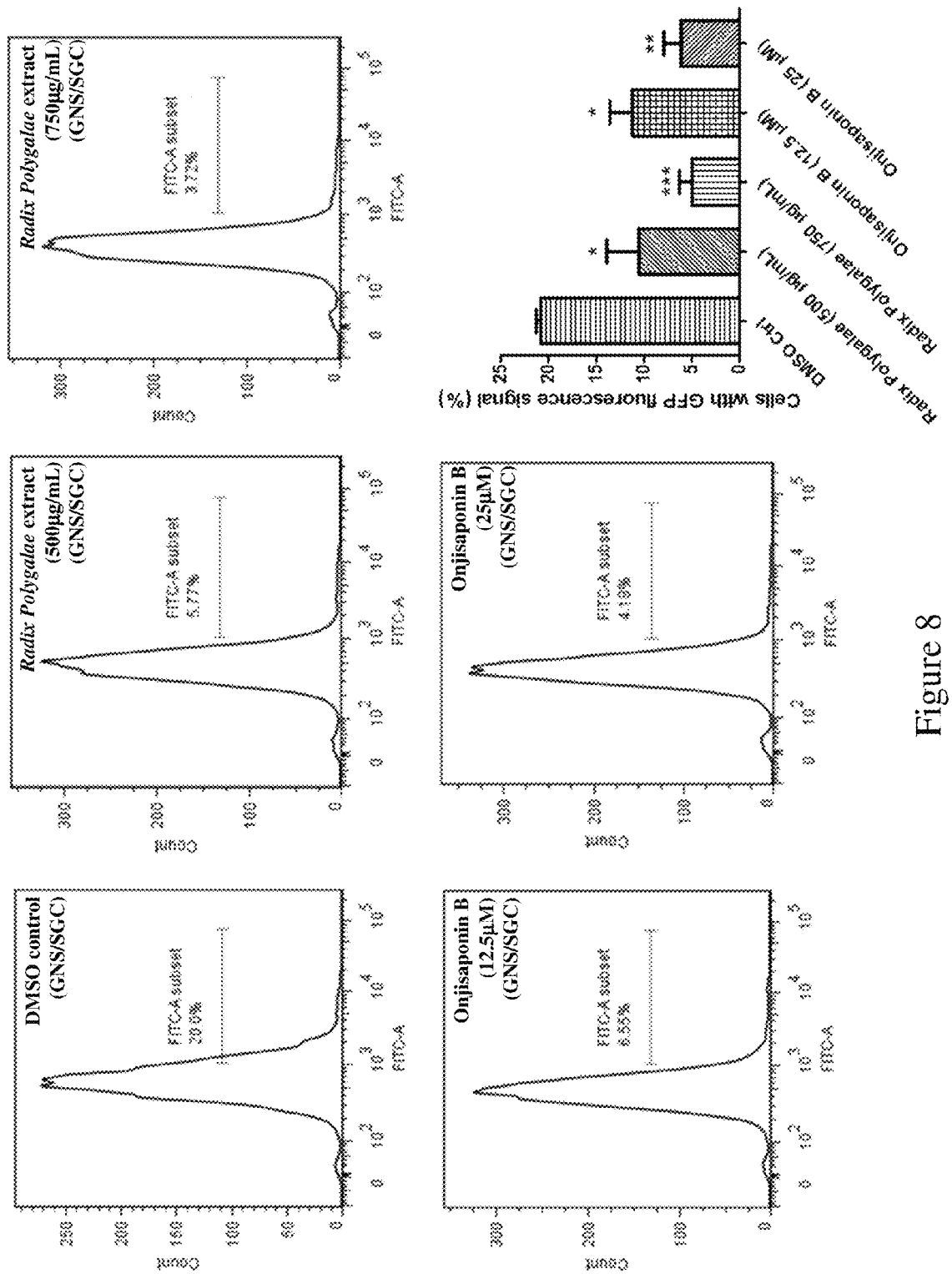
FIG. 8 shows that Onjisaponin B inhibits oligomerization of α-synuclein.

Results: By using the bimolecular fluorescence complementation (BiFC) assay, the oligomerization of α-synuclein in living cells [31] can be directly quantified. In brief, α-synuclein proteins fused with two different non-fluorescent GFP terminal fragments, (i) GFP-N terminal-α-synuclein (GNS) or (ii) α-synuclein-GFP-C terminal (SGC) respectively were used [31, 32]. Upon oligomerization of α-synuclein, the two non-fluorescent fractions of GFP will therefore reconstitute the complete GFP fluorophore and transmit GFP fluorescent signal within cells. This signal in turn can be quantified by flow cytometry analysis. As measured by flow analysis as shown in FIG. 8, both Radix Polygalae crude extract and Onjisaponin B inhibit the oligomerization of α-synuclein in HeLa cells transfected with GNS and SGC.

Conclusion: From the result, the decrease of GFP fluorescent signal suggested that both Radix Polygalae ethanol extract and its active component Onjisaponin B may play a protective role in Parkinson's disease through inhibiting α-synuclein oligomerization, which is a crucial step for α-synuclein aggregation. Taken together, these novel findings provide evidence to further support the neuroprotective function of Radix Polygalae ethanol extract and Onjisaponin B in cellular model.

EXAMPLE 8

This example describes an in vitro study to demonstrate that Onjisaponin B reduces toxicity in PC-12 cells expressing either mutant huntingtin or mutant A53T α-synuclein.

Cell cytotoxicity assay: Cytotoxicity was assessed using the 344,5-dimethylthiazol-2-yl)-2,5-diphenyltetrazolium bromide assay as described previously [28]. PC-12 cells were transfected with or without mutant huntingtin EGFP-HDQ74 for 24 h. The PC-12 cells were then seeded on 96-well plates with 4000 cells per well and then exposed to the indicated concentrations of Onjisaponin B (25 µmol/L) for 2 days. Subsequently, 10 µL of MTT reagents was added to each well and incubated at 37° C. for 4 hours, followed by the addition of 100 µL solubilization buffer (10% SDS in 0.01 mol/L HCl) and overnight incubation. Absorbance at 585 nm was determined from each well on the next day. The percentage of cell viability was calculated using the following formula: Cell viability (%)=Cells number treated/Cells number DMSO control×100. Data was obtained from three independent experiments.

Flow cytometry analysis: Doxycycline-inducible PC-12 cell lines transfected with mutant A53T α-synuclein were induced with doxycycline (1 µg/mL) for 24 h and the expression of transgene was then switched off by the removal of doxycycline. Cells were then treated with Onjisaponin B (50

μM) for a further 24 h after doxycycline removal. The control group (Ctrl) contained cells without the addition of doxycycline, while the Dox group contained cells with the removal of doxycycline (1 μg/mL) after 24 h of induction but without treatment of Onjisaponin B. Cell death was then assessed by flow cytometry using Annexin V staining kit and Propidium iodide staining. Data from the bar chart represented the means±S.D. of three independent experiments. **p<0.01; *p<0.05. Flow cytometry was carried out using a FACSCalibur flow cytometer. Data acquisition and analysis were performed with CellQuest.

Figure 9A:
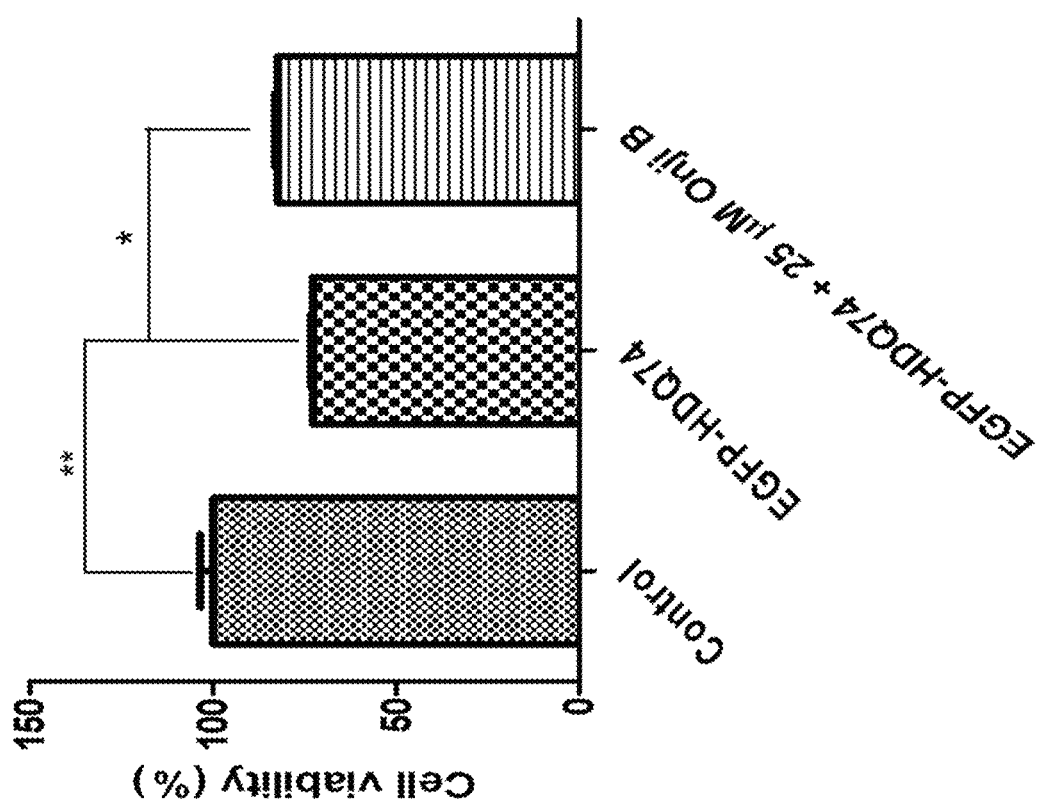
FIG. 9a and FIG. 9b show that Onjisaponin B reduces toxicity in PC-12 cells expressing either mutant huntingtin or mutant A53T α-synuclein.
Figure 9B:
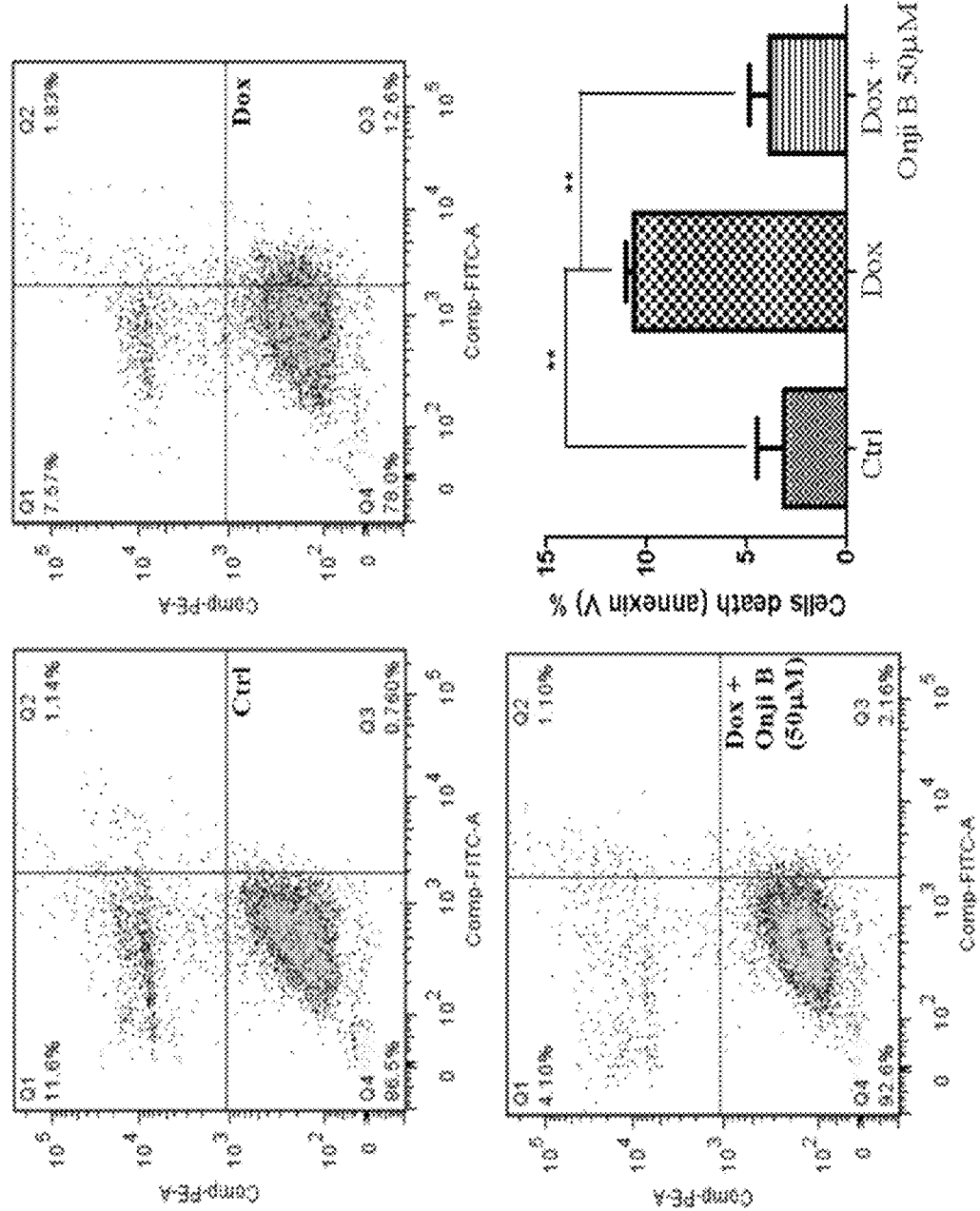

Results: With the result that Onjisaponin B treatment enhanced the clearance of mutant aggregate-prone proteins, Onjisaponin B was studied to see if it plays a protective role in reducing cell death induced by mutant huntingtin or mutant A53T α-synuclein expression. To study the toxicity of mutant huntingtin or mutant A53T α-synuclein in cells, PC-12 cells transfected transiently with EGFP-HDQ 74 or myc-tagged mutant A53T α-synuclein were used to examine the effect of Onjisaponin B on cell viability. As shown in FIGS. 9a and 9b, while transient expression of mutant huntingtin or mutant A53T α-synuclein lead to a decrease in cell viability, the addition of Onjisaponin B reduced toxicity in PC-12 cells expressing either mutant huntingtin (as shown in FIG. 9a) or mutant A53T α-synuclein (as shown in FIG. 9b), respectively.

Conclusion: In consistent with the results from the above Examples that Onjisaponin B increases the clearance of mutant huntingtin and mutant A53T α-synuclein and reduces oligomerization of α-synuclein, the result of this Example further demonstrated the potential therapeutic role of onjisaponin B working as a neuroprotective agent, through lowering of mutant huntingtin and α-synuclein toxicity in cells.

Brief Summary of Studies Described in Examples 1 to 8

In summary, throughout these studies, Onjisaponin B is proven to show no in vitro toxicity and possess autophagic effect, which is further demonstrated to be Atg7-dependent. Also, the activation of autophagy by Onjisaponin B is demonstrated to be through an AMPK-mTOR signaling pathway. Onjisaponin B is further shown to be a useful neuroprotective agent through accelerating the clearance of mutant huntingtin and α-synuclein in vitro, in which such clearance requires the induction of autophagy in cells. In addition, Onjisaponin B is proven to inhibit the oligomerization of α-synuclein and reduce toxicity in PC-12 cells expressing either mutant huntingtin or mutant A53T α-synuclein.

Taken together, these findings provide evidence to further support the neuroprotective function of Onjisaponin B and its medical application in treating neurodegenerative disease.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

References
1. Levine B, Kroemer G. Autophagy in the pathogenesis of disease. Cell 2008 Jan. 11; 132 (1): 27-42.
2. Law B Y, Wang M, Ma D L, Al-Mousa F, Michelangeli F, Cheng S H, et al. Alisol B, a novel inhibitor of the sarcoplasmic/endoplasmic reticulum Ca(2+) ATPase pump, induces autophagy, endoplasmic reticulum stress, and apoptosis. Mol Cancer Ther March; 9 (3): 718-730.
3. Rubinsztein D C. The roles of intracellular protein-degradation pathways in neurodegeneration. Nature 2006 Oct. 19; 443 (7113): 780-786.
4. Rubinsztein D C, DiFiglia M, Heintz N, Nixon R A, Qin Z H, Ravikumar B, et al. Autophagy and its possible roles in nervous system diseases, damage and repair. Autophagy 2005 April; 1 (1): 11-22.
5. Rubinsztein D C, Gestwicki J E, Murphy L O, Klionsky D J. Potential therapeutic applications of autophagy. Nat Rev Drug Discov 2007 April; 6 (4): 304-312.
6. Ravikumar B, Duden R, Rubinsztein D C. Aggregate-prone proteins with polyglutamine and polyalanine expansions are degraded by autophagy. Hum Mol Genet 2002 May 1; 11 (9): 1107-1117.
7. Ravikumar B, Vacher C, Berger Z, Davies JE, Luo S, Oroz LG, et al Inhibition of mTOR induces autophagy and reduces toxicity of polyglutamine expansions in fly and mouse models of Huntington disease. Nat Genet 2004 June; 36 (6): 585-595.
8. Webb J L, Ravikumar B, Atkins J, Skepper J N, Rubinsztein DC. Alpha-Synuclein is degraded by both autophagy and the proteasome. J Biol Chem 2003 Jul. 4; 278 (27): 25009-25013.
9. Rubinsztein D C, Codogno P, Levine B. Autophagy modulation as a potential therapeutic target for diverse diseases. Nat Rev Drug Discov September; 11 (9): 709-730.
10. Rubinsztein D C. Lessons from animal models of Huntington's disease. Trends Genet 2002 April; 18 (4): 202-209.
11. Sarkar S, Davies J E, Huang Z, Tunnacliffe A, Rubinsztein D C. Trehalose, a novel mTOR-independent autophagy enhancer, accelerates the clearance of mutant huntingtin and alpha-synuclein. J Biol Chem 2007 Feb, 23; 282 (8): 5641-5652.
12. Sarkar S, Floto R A, Berger Z, Imarisio S, Cordenier A, Pasco M, et al. Lithium induces autophagy by inhibiting inositol monophosphatase. J Cell Biol 2005 Sep, 26; 170 (7): 1101-1111.
13. Berger Z, Ravikumar B, Menzies F M, Oroz L G, Underwood B R, Pangalos M N, et al. Rapamycin alleviates toxicity of different aggregate-prone proteins. Hum Mol Genet 2006 Feb. 1; 15 (3): 433-442.
14. Wong E, Cuervo A M. Autophagy gone awry in neurodegenerative diseases. Nat Neurosci July; 13 (7): 805-811.
15. Renna M, Jimenez-Sanchez M, Sarkar S, Rubinsztein D C. Chemical inducers of autophagy that enhance the clearance of mutant proteins in neurodegenerative diseases. J Biol Chem Apr. 9; 285 (15): 11061-11067.
16. Jia K, Levine B. Autophagy is required for dietary restriction-mediated life span extension in *C. elegans*. Autophagy 2007 November-December; 3 (6): 597-599.
17. Jia K, Hart A C, Levine B. Autophagy genes protect against disease caused by polyglutamine expansion proteins in *Caenorhabditis elegans*. Autophagy 2007 January-February; 3 (1): 21-25.
18. Komatsu M, Waguri S, Chiba T, Murata S, Iwata J, Tanida I, et al. Loss of autophagy in the central nervous system causes neurodegeneration in mice. Nature 2006 Jun. 15; 441 (7095): 880-884.
19. Hara T, Nakamura K, Matsui M, Yamamoto A, Nakahara Y, Suzuki-Migishima R, et al. Suppression of basal autophagy in neural cells causes neurodegenerative disease in mice. Nature 2006 Jun. 15; 441 (7095): 885-889.
20. Komatsu M, Wang Q J, Holstein G R, Friedrich V L, Jr., Iwata J, Kominami E, et al. Essential role for autophagy protein Atg7 in the maintenance of axonal homeostasis and the prevention of axonal degeneration. Proc Natl Acad Sci USA 2007 Sep. 4; 104 (36): 14489-14494.
21. Yang F, Lim G P, Begum A N, Ubeda O J, Simmons M R, Ambegaokar S S, et al. Curcumin inhibits formation of amyloid beta oligomers and fibrils, binds plaques, and reduces amyloid in vivo. J Biol Chem 2005 Feb. 18; 280 (7): 5892-5901.
22. Zhao Z, Fang M, Xiao D, Liu M, Fefelova N, Huang C, et al. Potential antiarrhythmic effect of methyl 3,4,5-trimethoxycinnamate, a bioactive substance from roots of polygalae radix: suppression of triggered activities in rabbit myocytes. Biol Pharm Bull; 36 (2): 238-244.
23. Zhang H, Han T, Zhang L, Yu C H, Wan D G, Rahman K, et al. Effects of tenuifolin extracted from radix polygalae on learning and memory: a behavioral and biochemical study on aged and amnesic mice. Phytomedicine 2008 August; 15 (8): 587-594.
24. Lin Z, Gu J, Xiu J, Mi T, Dong J, Tiwari J K. Traditional chinese medicine for senile dementia. Evid Based Complement Alternat Med; 2012: 692621.
25. Xie W, Yang Y, Gu X, Zheng Y, Sun Y E, Liang Y, et al. Senegenin attenuates hepatic ischemia-reperfusion induced cognitive dysfunction by increasing hippocampal NR2B expression in rats. PLoS One; 7 (9): e45575.
26. Choi J G, Kim H G, Kim M C, Yang W M, Huh Y, Kim S Y, et al. Polygalae radix inhibits toxin-induced neuronal death in the Parkinson's disease models. J Ethnopharmacol March 24; 134 (2): 414-421.
27. Karakida F, Ikeya Y, Tsunakawa M, Yamaguchi T, Ikarashi Y, Takeda S, et al. Cerebral protective and cognition-improving effects of sinapic acid in rodents. Biol Pharm Bull 2007 March; 30 (3): 514-519.
28. Wong V K, Zhou H, Cheung S S, Li T, Liu L. Mechanistic study of saikosaponin-d (Ssd) on suppression of murine T lymphocyte activation. J Cell Biochem 2009 May 15; 107 (2): 303-315.
29. Sarkar S, Perlstein E O, Imarisio S, Pineau S, Cordenier A, Maglathlin R L, et al. Small molecules enhance autophagy and reduce toxicity in Huntington's disease models. Nat Chem Biol 2007 June; 3 (6): 331-338.
30. Talloczy Z, Virgin H Wt, Levine B. PKR-dependent autophagic degradation of herpes simplex virus type 1. Autophagy 2006 January-March; 2 (1): 24-29.
31. Outeiro T F, Putcha P, Tetzlaff J E, Spoelgen R, Koker M, Carvalho F, et al. Formation of toxic oligomeric alpha-synuclein species in living cells. PLoS One 2008; 3 (4): e1867.
32. Lu J H, Ardah M T, Durairajan S S, Liu L F, Xie L X, Fong W F, et al. Baicalein inhibits formation of alpha-synuclein oligomers within living cells and prevents Abeta peptide fibrillation and oligomerisation. Chembiochem March 7; 12 (4): 615-624.

What is claimed is:

1. A method of treating a human suffering from Huntington's disease comprising administering a therapeutically effective amount of an isolated Onjisaponin B to the human to effectively treat the Huntington's disease in the human.

* * * * *